United States Patent [19]

Lukàc et al.

[11] Patent Number: 4,701,540

[45] Date of Patent: Oct. 20, 1987

[54] PROCESS FOR CAROTENOID INTERMEDIATES

[75] Inventors: Teodor Lukàc, Aesch; Milan Soukup, Stein; Erich Widmer, Münchenstein, all of Switzerland

[73] Assignee: Hoffmann-La Roche Inc., Nutley, N.J.

[21] Appl. No.: 588,268

[22] Filed: Mar. 12, 1984

[30] Foreign Application Priority Data

Mar. 25, 1983 [CH]  Switzerland ................ 1646/83

[51] Int. Cl.[4] ............... C07D 317/20; C07D 317/72; C07C 37/00; C07C 43/184
[52] U.S. Cl. ............................ 549/341; 549/453; 549/362; 568/361; 568/363; 568/420; 568/579; 568/591; 568/668; 568/447; 568/670; 568/824; 568/828; 568/825; 568/838
[58] Field of Search .................. 549/341, 362, 453; 568/668, 447, 828, 361, 363, 420, 579, 670, 828, 838, 824, 825, 591

[56] References Cited

U.S. PATENT DOCUMENTS

| | | | |
|---|---|---|---|
| 2,655,548 | 10/1953 | Evans et al. | 568/828 |
| 2,671,112 | 3/1954 | Inhoffen et al. | 568/668 |
| 2,705,728 | 4/1955 | Inhoffen | 568/668 |
| 2,798,101 | 7/1957 | Inhoffen | 568/447 |
| 4,156,090 | 5/1979 | Kienzle | 549/341 |

FOREIGN PATENT DOCUMENTS 518891  2/1972  Switzerland .

OTHER PUBLICATIONS

Mayer et al., Helv. Chim. Acta 59, 1424 (1976).
Widmer et al., Helv. Chim. Acta 65, 958 (1982).
Widmer et al., Helv. Chim. Acta 64, 2436 (1981).
Widmer, Manuscript B-110'128, Lecture at the 29th IUPAC Congress (Cologne, Germany) (1983).

*Primary Examiner*—Nicky Chan
*Attorney, Agent, or Firm*—Jon S. Saxe; George M. Gould; William H. Epstein

[57] ABSTRACT

A process for producing cycloketones of a 5 or 6 carbon chain length through which said ketones are known intermediates for producing carotenoids.

13 Claims, No Drawings

PROCESS FOR CAROTENOID INTERMEDIATES

SUMMARY OF THE INVENTION

The process in accordance with the invention comprises reacting a cyclic ketone of the formula

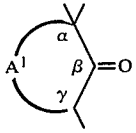   I wherein $A^1$ is a chain of from 2 or 3 carbon atoms optionally substituted by 1 or 2 ether groups, the ends of the chain being linked with the carbon atoms in the α- and γ-positions
with a lithium salt of the general formula

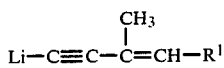   II wherein $R^1$ is $-CHR^2R^3$ or $-CH_2OLi$, $R^2$ is hydrogen or ether and $R^3$ is ether,
in an inert organic solvent, reducing the resulting compound of the formula

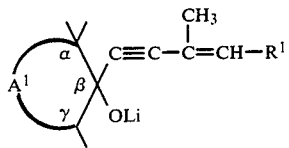   III wherein $A^1$ and $R^1$ are as above,
with an aluminium hydride of the formula

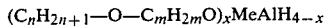   IV wherein Me is an alkali metal, x is a number of from 1 to 3 and m and n each are a number of from 1 to 7,
and subsequently hydrolyzing the resulting aluminium complex to give a compound of the formula

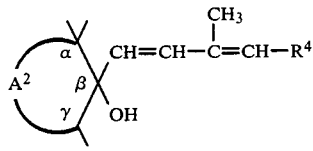   V wherein $R^4$ is $-CHR^2R^3$, $-CH_2OH$ or $-CHO$, $R^2$ and $R^3$ are as above, $A^2$ is a chain of from 2 or 3 carbon atoms optionally substituted by 1 or 2 hydroxy or ether groups or an oxo group and the ends of the carbon chain $A^2$ are linked with the carbon atoms in the α- and γ-position,
and, if desired, dehydrating a resulting compound of formula V in which group $A^2$ is linked with the carbon atom in the γ-position via a single covalent bond to give a compound of the general formula

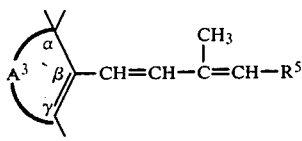   VI wherein $R^5$ is $-CH_2OH$ or $-CHO$, $A^3$ is a chain of 2 or 3 carbon atoms which is optionally substituted by 1 or 2 hydroxy group or an oxo group and the ends of the carbon chain $A^3$ are linked with the carbon atoms in the α- and γ-position.

The compounds of formula V and VI are known intermediates for carotenoids or analogs of known intermediates.

DETAILED DESCRIPTION

Group $A^1$ above embraces within its definition the divalent hydrocarbon groups $-CH_2-CH_2-$, $-CH_2-CH=$, $-CH=CH-$, $-CH_2-CH_2-CH_2-$, $-CH_2-CH_2-CH=$, $-CH_2-CH=CH-$, $-CH=CH-CH_2-$ and $-CH=CH-CH=$ and the groups derived therefrom in which 1 or 2 hydrogen atoms have been replaced by ether groups. The compounds of formula I accordingly contain a carbocyclic 5-membered or 6-membered ring. The significance of groups $A^2$ and $A^3$ follows accordingly, bearing in mind that in the cleavage of ether groups there are formed the corresponding hydroxy compounds or in the case of geminal diethers (ketals) the corresponding carbonyl compounds and that enols can rearrange to corresponding ketones.

The term "ether group" used above in connection with $A^1$, $A^2$ and $R^1$ embraces all ether groups used as protecting groups for alcohols and ketones. Examples of such groups are benzyloxy, tetrahydropyranyloxy, $C_1$-$C_7$-alkoxy (e.g. methoxy, t-butoxy, isobutoxy), silyloxy groups (e.g. trimethylsilyloxy), groups of the general formula

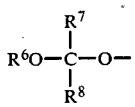   VII wherein $R^6$ is $C_1$-$C_7$-alkyl and $R^7$ and $R^8$ is hydrogen or $C_1$-$C_7$-alkyl,
(e.g. 1-methoxy-1-methylethoxy) and the like. In the case of geminal and vicinal diethers the two ether groups together can also form a cyclic group. Such groups are present, for example, when a ketone or aldehyde is protected by ketalization or acetalization with a diol, preferably with ethylene glycol or butane-2,3-diol, when a vicinal diol is protected by ketalization with a ketone, preferably with acetone, or when an enolized α-hydroxyketone is protected by etherification to the dimer. Examples of preferred ether groups are methoxy, isobutoxy and 1-methoxy-1-methylethoxy as well as in the case of geminal diethers also ethylenedioxy and in the case of vicinal diethers also the acetonide group. Further, in the case of compounds of formula I derived from enolized α-hydroxyketones (e.g. 3,4-dihydroxy-2,5,5-trimethyl-2-cyclopenten-1-one) there are also preferred the vicinal diethers formed by etherification to the dimer.

As seen from the above, the chains $A^1$ and $A^2$ are hydrocarbon chains of 2 to 3 carbon atoms which can be unsubstituted or substituted with a hydroxy or oxo group where the hydroxy or oxo group is protected by means of a hydrolyzable ether as described above. These hydrolyzable ether groups can be removed by conventional hydrolysis to generate hydroxy or oxo moieties.

The term "alkali metal" signifies in the scope of the present invention lithium, sodium and potassium, especially lithium and sodium.

The process in accordance with the invention provides an elegant method for the manufacture of the compounds of formulae V and VI in high yield. Since the alkynylation and the subsequent reduction and hydrolysis, as well as optionally also the dehydration, can be carried out as a one-pot reaction, a time-consuming and expensive working-up of the intermediates is unnecessary. Further, since the intermediate salts of formula III complex with the compounds of formula IV surprisingly rapidly and without problems, the reduction is effected almost instantaneously and with comparatively small amounts of reducing agent even under mild conditions.

$A^1$ in formula I above preferably represents the group $CH_2-CH=$, $-CH_2-CH_2-CH_2-$, $-CH_2-CH_2-CH=$ or $-CH=CH-CH=$ or a group derived therefrom in which 1 or 2 hydrogen atoms have been replaced by ether groups. Especially preferred starting materials for the process in accordance with the invention are those compounds of formula I in which $A^1$ represents the group $-CHR-CR'=$, $-CH_2-CR=$, $-CH_2-CH_2-CH_2-$, $-CH_2-CHR-CH_2-$, $-CH_2-CRR'-CH_2-$, $-CH_2-CH_2-CR=$, $-CH_2-CHR-CR'=$ or $-CH_2-CRR'-CH=$ wherein R and R' represents hydroxy protected by a hydrolizable ether group or geminal R and R' taken together form oxo protected through hydrolizable ether groups. Examples of especially preferred starting materials of formula I are:

4-(1-methoxy-1-methylethoxy)-2,2,6-trimethylcyclohexan-1-one;
7,9,9-trimethyl-1,4-dioxaspiro[4.5]dec-6-en-8-one;
7,7,9-trimethyl-1,4-dioxaspiro[4.5]decan-8-one;
2,2,4,6,6-pentamethyl-7,7a-dihydro-2H,6H,1,3-benzodioxol-5-one;
2,2,6-trimethyl-5-isobutoxy-5-cyclohexen-1-one;
2,2,6-trimethylcyclohexanone; and
cis-1,4a,5,8a-tetrahydro-1,1,3,5,5,7-hexamethyldicyclopenta-b-dioxin-2,6-dione.

The 3-or 4-stage process in accordance with the invention is carried out in an inert organic solvent, for example in an ether or a saturated or aromatic hydrocarbon such as tetrahydrofuran, dioxan, diethyl ether, petroleum ether, hexane, benzene, toluene, xylene and the like. Tetrahydrofuran is the preferred solvent.

The alkynylation of a ketone of formula I with a lithium salt of formula II can be carried out in a manner known per se. In carrying out this reaction, temperature and pressure are not critical. However, the alkynylation is generally carried out at atmospheric pressure and at room temperature or at a lower temperature, preferably at about $-30°$ C. to room temperature. The alkynylation can be carried out using equimolar amounts of compounds of formula I and II. However, a slight excess of the compound of formula II is generally preferred.

The reduction of the lithium alcoholate of formula III can be carried out under the usual conditions which are normally used in the case of reductions with aluminium hydrides of formula IV. The temperature and pressure are not critical and the reaction can be carried out at room temperature. Since, however, the present reduction takes place rapidly even at low temperatures, the reduction is preferably carried out at about $-50°$ C. to room temperature ($30°$ C.). The reduction is conveniently carried out by adding the reducing agent to the reaction mixture obtained immediately after completion of the alkynylation reaction. In general, the triple bond in formula III is reduced almost exclusively to the trans double bond. Me in formula IV preferably represents lithium or sodium. Further, those reducing agents of formula IV in which x represents the number 2 are preferred. In the formula IV m and n preferably each represent a number of 1 to 3. Sodium bis(2-methoxyethoxy) aluminium hydride is the especially preferred reducing agent. There are generally used about equivalent amounts of compounds of formulae III and IV or, preferably, a slight excess of the compound of formula IV.

The subsequent hydrolysis of the intermediate aluminium complex and the optional dehydration of a compound of formula V, wherein $A^2$ is linked with the carbon atom in the $\gamma$-position via a single covalent bond to give a compound of formula VI can be carried out according to hydrolysis and dehydration methods known per se using usual reagents. The optimum conditions can vary according to the substrate, protecting groups and desired product, but can be determined readily on a case to case basis.

The hydrolysis of the intermediate aluminium complex can be carried out, for example, with water, with aqueous ammonium chloride solution, acetate buffer solution or phosphate buffer solution, with alkalis such as sodium hydroxide or potassium hydroxide, with organic or inorganic acids such as p-toluenesulfonic acid, sulfuric acid and the like. If desired, the hydrolysis can be carried out in such a manner that the optionally present ether groups are also hydrolyzed simultaneously. The conditions under which the protecting groups used here remain or are cleaved off are in principle known to the person skilled in the art. In general, however, it can be said that the protecting groups remain under neutral or basic conditions and occasionally under weak acidic conditions, while they are cleaved off under acidic conditions, especially under strong acidic conditions. The temperature and pressure are not critical. However, the hydrolysis is generally carried out at atmospheric pressure and at room temperature or at a lower temperature, preferably at about $0°$ C. to room temperature.

The dehydration of a compound of formula V in which group $A^2$ is linked with the carbon atom in the $\gamma$-position via a single covalent bond to give a compound of formula VI can be carried out with usual dehydrating reagents which are known in the literature, for example with strong organic or inorganic acids such as p-toluenesulfonic acid, sulfuric acid and the like. The optimum conditions can vary according to the substrate. However, atmospheric pressure and a temperature from room temperature to the reflux temperature are generally preferred. A preferred method for the manufacture of the compound of formula VI comprises treating the aluminium complex obtained after the reduction with a strong organic or inorganic acid under the conditions given for the dehydration, by which means hydrolysis of the complex, cleavage of protecting groups which may be present and dehydration can be achieved in one step. On the other hand, in the case of certain compounds of formula V which are difficult to dehydrate, it can be advantageous to convert these firstly into derivatives which can be dehydrated more readily. For example, the dehydration of 5-[1,4-dihydroxy-2,2,6-trimethylcyclohexyl]-3-methyl-2,4-pentadien-1-ol is facilitated when this is firstly esterified to the diacetate.

The starting materials of formulae I and II are known or are analogues of known compounds and can be prepared in a known manner or in a manner known per se.

The acetylenides of formula II can advantageously be prepared in situ from the corresponding acetylene derivative by reaction with a suitable lithium compound, for example phenyl lithium or an alkyl lithium such as methyl lithium, butyl lithium and the like. This reaction is conveniently carried out at atmospheric pressure and at about $-30°$ C. to room temperature in the same solvent which is subsequently used for the process in accordance with the invention.

The invention is further concerned with all novel compounds, mixtures, processes and uses as herein described.

The following Examples illustrate the process in accordance with the invention.

EXAMPLE 1

14.5 g of 5-(1-methoxy-1-methylethoxy)-3-methyl-3E-penten-1-yne (95%, 83 mmol) were dissolved in 90 ml of tetrahydrofuran in a sulfonation flask provided with a stirrer, thermometer and dropping funnel with pressure balance while gassing with argon and cooled with an acetone/dry-ice bath $-15°$ C. At this temperature there was added while cooling well within 30 minutes a solution of 60 ml of a 1.4M solution of butyl lithium (80 mmol) in hexane and the mixture was then stirred at $0°$ C. under argon for a further 30 minutes. A solution of 4(R)-(1-methoxy-1-methylethoxy)-2,2,6(R)-trimethylcyclohexan-1-one in tetrahydrofuran was subsequently added dropwise within 30 minutes while stirring, gassing with argon and cooling at $-10°$ C., the cooling bath was then removed and the reaction mixture was warmed carefully to room temperature and stirred for 1 hour.

The reaction mixture was cooled to $-10°$ C. Subsequently, 25 ml of a 70% (wt.%) solution of sodium bis(1-methoxyethoxy)aluminium hydride (90 mmol) in toluene were treated with 75 ml of tetrahydrofuran and the solution obtained was added to the reaction mixture within 15 minutes. The reaction mixture was stirred at $-10°$ C. for a further 15 minutes.

Subsequently, the reaction mixture was treated with 50 ml of ethanol at $-10°$ C. while stirring vigorously within 5 minutes, then treated dropwise with 200 ml of 3N sulfuric acid within 10 minutes while cooling well and finally stirred at $0°$ C. for a further 1 hour. Three separating funnels $S_1-S_3$ were each charged with 150 ml of ethyl acetate. Then, firstly the reaction mixture and then three 150 ml portions of semi-saturated aqueous sodium hydrogen carbonate solution were passed in sequence and with good intermixing through the three separating funnels $S_1-S_3$. The aqueous phases were discarded. The organic phases were combined and dried over sodium sulfate. The drying agent was filtered off, rinsed with 50 ml of ethyl acetate and the filtrate was dried to constant weight in a rotary evaporator under a water-jet vacuum at $40°$ C., 24.0 g of a semi-crystalline yellow mass being obtained as the residue. This crude product was dissolved in 90 ml of ethyl acetate on a steam-bath under reflux until clear, then cooled slowly to room temperature while stirring and stored at $-20°$ C. overnight. The crystallized-out product was filtered off under suction, washed twice with 10 ml of cold ($-20°$ C.) ethyl acetate each time and dried to constant weight in a drying oven under a water-jet vacuum at $40°$ C. There were thus obtain 9.6 g of colorless crystals of melting point $156°-161°$ C., $\alpha_D = -56.6°$. The mother liquor was evaporated in a rotary evaporator under a water-jet vacuum and then largely freed from 3-methyl-2-penten-4-yn-1-ol in a high vacuum. The residual oil (9.4 g) was crystallized from 30 ml of ethyl acetate in an analogous manner to the first crystallization, there being obtained a further 0.6 g of product in the form of colorless crystals of melting point $153°-159°$ C. Total yield: 10.2 g [67% based on 4(R)-hydroxy-2,2,6(R)-trimethylcyclohexan-1-one] of 5-[1(R,S),4(R)-dihydroxy-2,2,6(R)-trimethylcyclohexyl]-3-methyl-2E,4E-pentadien-1-ol (1R/1S ratio 95:5) which was pure according to thin-layer chromatography.

The solution of 4(R)-(1-methoxy-1-methylethoxy)-2,2,6(R)-trimethylcyclohexan-1-one in tetrahydrofuran used above was prepared as follows:

A solution of 9.4 g of 4(R)-hydroxy-2,2,6(R)-trimethylcyclohexan-1-one (60 mmol) in 50 mol of tetrahydrofuran was placed in a solfonation flask provided with a stirrer, thermometer and dropping funnel with pressure balance and cooled to $15°$ C. while gassing with argon and stirring. After adding 20 mg of p-toluenesulfonic acid monohydrate, 8.7 g of isopropenyl methyl ether (120 mmol) were added dropwise within 45 minutes at $15°-20°$ C. (cooling with a methanol/ice bath). the resulting solution of 4(R)-(1-methoxy-1-methylethoxy)-2,2,6(R)-trimethylcyclohexan-1-one was treated with 0.2 ml of triethylamine, cooled to $-10°$ C. and stored under argon until used.

EXAMPLE 2

24.1 g of 5,5-dimethoxy-3-methyl-3Z-penten-1-yne (166 mmol) were dissolved in 150 ml of absolute tetrahydrofuran in a sulfonation flask provided with a stirrer, thermometer and dropping funnel with pressure balance while gassing with argon and the solution was cooled with an acetone/dry-ice bath to $-15°$ C. At this temperature there were added while cooling well within 30 minutes 120 ml of a 1.4M solution of butyl lithium (160 mmol) in hexane and the resulting lithium salt solution was stirred at $0°$ C. for a further 30 minutes. A solution of 23.8 g of 7,9,9-trimethyl-1,4-dioxaspiro[4,5]-dec-6-en-8-one (120 mmol) in 100 ml of tetrahydrofuran was subsequently added dropwise to the reaction mixture within 15 minutes while stirring, gassing with argon and cooling at $-10°$ C. The cooling bath was then removed and the reaction mixture was warmed carefully to room temperature and stirred for 2 hours.

The reaction mixture was cooled to $-45°$ C. Subsequently, 50 ml of a 70% (wt.%) solution of sodium bis(2-methoxyethoxy)aluminium hydride (180 mmol) in toluene were treated with 140 ml of tetrahydrofuran and the solution obtained was added dropwise to the reaction mixture within 15 minutes.

Subsequently, the reaction mixture was treated dropwise with 100 ml of ethanol at −45° C. while stirring vigorously within 10 minutes, then treated with 300 ml of semi-saturated aqueous ammonium chloride solution at −10° C. to 0° C. and stirred at 0° C. for a further 1 hour. Three separating funnels $S_1$–$S_3$ were each charged with 250 ml of ethyl acetate. Then, firstly the reaction mixture and then three 200 ml portions of semi-saturated aqueous sodium chloride solution were passed in sequence and with good intermixing through the separating funnels $S_1$–$S_3$. The aqueous phases were discarded. The organic phases were combined and dried over sodium sulfate. The drying agent was filtered off and rinsed with 80 ml of ethyl acetate. The filtrate was concentrated in a rotary evaporator under a water-jet vacuum at 40° C. and largely freed from 5,5-dimethoxy-3-methyl-3Z-penten-1-yne in a high vacuum (3 hours at 50° C./0.015 mm Hg). As the residue there were obtained 43.2 g of crude 8-(5,5-dimethoxy-3-methyl-1E,3Z-pentadienyl)-8-hydroxy-7,9,9-trimethyl-1,4-dioxaspiro[4,5]dec-6-ene in the form of a yellowish oil.

The oil obtained was dissolved in 80 ml of acetone and 50 ml of deionized water in a flask provided with a thermometer. magnetic stirrer and argon gasification. After adding 0.2 g of p-toluenesulfonic acid, the reaction mixture was stirred at room temperature for 45 minutes. Three separating funnels $S_1$–$S_3$ were each charged with 200 ml of ethyl acetate. Then, firstly the reaction mixture and then three 80 ml portions of saturated aqueous sodium hydrogen carbon solution were passed in sequence and with good intermixing through the separating funnels $S_1$–$S_3$. The aqueous phases were discarded. The organic phases were combined and dried over sodium sulfate. The drying agent was filtered off and rinsed with 60 ml of ethyl acetate. The filtrate was evaporated to constant weight on a rotary evaporator under a water-jet vacuum at 40° C., 35.8 g of a yellowish oil remaining behind. The oil obtained was dissolved in 100 ml of diisopropyl ether and 10 ml of ethyl acetate on a steam-bath under reflux, then cooled slowly to room temperature while stirring and left to stand at −20° C. overnight. The crystallized-out product was filtered off under suction, washed on the filter twice with 20 ml of cold (−20° C.) diisopropyl ether each time and dried to constant weight in a drying oven under a water-jet vacuum at 40° C. There were thus obtained 20.9 g (70.1%) of 5-(1-hydroxy-4-oxo-2,6,6-trimethyl-2-cyclohexenyl)-3-methyl-2Z,4E-pentadienal in the form of colorless crystals of melting point 111°–113° C.

EXAMPLE 3

14.7 g of 5-(1-methoxy-1-methylethoxy)-3-methyl-3Z-penten-1-yne (83 mmol) were dissolved in 90 ml of absolute tetrahydrofuran in a sulfonation flask provided with a stirrer, thermometer and dropping funnel with pressure balance while gassing with argon and the solution was cooled with an acetone/dry-ice bath to −15° C. At this temperature there were added to the reaction mixture within 10 minutes while cooling well 60 ml of a 1.4M solution of butyl lithium (80 mmol) in hexane and the resulting lithium salt solution was stirred at 0° C. under argon for a further 30 minutes. A solution of 11.9 g of 7,9,9-trimethyl-1,4-dioxaspiro[4.5]dec-6-en-8-one (60 mmol) in 60 ml of tetrahydrofuran was subsequently added dropwise to the reaction mixture within 8 minutes while stirring, gassing with argon and cooling at −10° C. The cooling bath was then removed and the reaction mixture was warmed carefully to room temperature and stirred for 1.5 hours.

The reaction mixture was cooled to −25° C. Subsequently, 14 ml of a 70% (wt. %) solution of sodium bis(2-methoxyethoxy)aluminium hydride (50.2 mmol) in toluene were treated with 80 ml of tetrahydrofuran and the solution obtained was added dropwise to the reaction mixture within 10 minutes. The cooling bath was then removed and the reaction mixture was warmed carefully to −10° C. and stirred for 30 minutes. Subsequently, the reaction mixture was treated dropwise with 30 ml of ethanol at −20° C. within 10 minutes, then treated with 200 ml of 3N sulphuric acid at about −10° C. to 15° C. and stirred at 15° C. to room temperature for a further 2 hours. Three separating funnels $S_1$–$S_3$ were each charged with 150 ml of ethyl acetate. Then, firstly the reaction mixture and then three 150 ml portions of saturated sodium hydrogen carbonate solution were passed in sequence and with good intermixing through the separating funnels $S_1$–$S_3$. The aqueous phases were discarded. The organic phases were combined and dried over sodium sulfate. The drying agent was filtered off and rinsed with 80 ml of ethyl acetate. The filtrate was concentrated in a rotary evaporator under a water-jet vacuum at 40° C. and finally largely freed from 3-methyl-2Z-penten-4-yn-1-ol in a high vacuum (2.5 hours at 55° C./0.1 mm Hg). As the residue there were obtained 19.5 g of crude 5-(1-hydroxy-4-oxo-2,6,6-trimethyl-2-cyclohexenyl)-3-methyl-2Z,4E-pentadien-1-ol in the form of a yellowish crystalline mass. The crude product obtained was dissolved in 25 ml of ethyl acetate and 25 ml of diisopropyl ether on a steam-bath under reflux, the solution was cooled slowly to room temperature while stirring and left to stand at −20° C. overnight. The crystallized-out product was filtered off under suction, washed on the filter twice with 15 ml of cold (−20° C.) diisopropyl ether each time and then dried to constant weight in a drying oven under a water-jet vacuum at 40° C. There were thus obtained 9.3 g (62%) of 5-(1-hydroxy-4-oxo-2,6,6-trimethyl-2-cyclohexenyl)-3-methyl-2Z,4E-pentadien-1-ol in the form of colorless crystals of melting point 127°–129° C.

EXAMPLE 4

24.0 g of 3-methyl-2Z-penten-4-yn-1-OL (249.6 mmol) were dissolved in 150 ml of absolute tetrahydrofuran in a sulfonation flask provided with a stirrer, thermometer and dropping funnel with pressure balance while gassing with argon and the solution was cooled with an acetone/dry-ice bath to −20° C. At this temperature there were added dropwise while cooling well within 20 minutes 308 ml of a 1.56M solution of butyl lithium (481.2 mmol) in hexane and the resulting dilithium salt (a beige suspension) was stirred at −10° C. under argon for a further 25 minutes. A solution of 23.8 g of 7,9,9-trimethyl-1,4-dioxaspiro-[4.5]dec-6-en-8-one (120 mmol) in 100 ml of tetrahydrofuran was subsequently added dropwise to the reaction mixture within 10 minutes while stirring, gassing with argon and cooling at −5° C. 2 g of tetrabutylammonium bromide (6.2 mmol) were then added to the reaction mixture, the cooling bath was removed and the mixture was warmed carefully to room temperature and stirred for 3.75 hours.

The reaction mixture was cooled to −25° C. Subsequently, 60 ml of a 70% (wt. %) solution of sodium bis(2-methoxyethoxy)aluminium hydride (215 mmol) in toluene were treated with 110 ml of tetrahydrofuran and the solution obtained was added dropwise to the reaction mixture within 10 minutes. The cooling bath was then removed and the reaction mixture was warmed carefully to room temperature (whereby the suspension dissolved and the color changed to claret) and stirred for 1 hour.

Subsequently, the reaction mixture was treated dropwise with 100 ml of ethanol at −20° C. within 10 minutes (whereby the color changed from claret to pale yellow), then treated with 500 ml of 3N sulfuric acid at about −10° C. to 12° C. and stirred at 12° C. to room temperature for a further 15 minutes. Three separating funnels $S_1$–$S_3$ were each charged with 400 ml of ethyl acetate. Then, firstly the reaction mixture and then three 250 ml portions of saturated sodium hydrogen carbonate solution were passed in sequence and with good intermixing through the separating funnels $S_1$–$S_3$. The aqueous phases were discarded. The organic extracts were combined and dried over sodium sulphate. The drying agent was filtered off and rinsed with 80 ml of ethyl acetate. The filtrate was evaporated in a rotary evaporator under a water-jet vacuum at 40° C. The residue obtained (44.1 g of yellowish crystals) was digested three times with 300 ml of pentane each time on a steam-bath under reflux. Before decanting off the pentane the mixture was each time cooled with an ice-/water bath. Concentration of the cooled pentane extracts in a rotary evaporator under a water-jet vacuum at 40° C. gave 11.6 g of a yellowish oil. The crystalline residue remaining behind in the digestion was also dried to constant weight in a rotary evaporator under a water-jet vacuum at 40° C., there being obtained 29.3 g of a yellowish crystalline crude product of 5-(1-hydroxy-4-oxo-2,6,6-trimethyl-2-cyclo-hexenyl)-3-methyl-2Z,4E-pentadien-1-ol. This crude product was dissolved in 70 ml of ethyl acetate on a steam-bath under reflux and the warm solution was treated dropwise with 35 ml of hexane while stirring within 10 minutes. The solution was then cooled to room temperature within 3 hours and left to stand at −20° C. overnight. The crystallized-out product was filtered off under suction, washed on the suction filter three times with 20 ml of cold (−20° C.) hexane each time and subsequently dired to constant weight in a drying oven under a water-jet vacuum at 40° C. There were thus obtained 24.0 g (80.0%) of colorless crystals of melting point 126°–128° C. Evaporation of the mother liquor in a rotary evaporator under a water-jet vacuum gave 5.3 g of a yellowish oil from which there could be isolated by chromatography and crystallization of the product fractions from ethyl acetate/hexane a further 0.8 g (2.6%) of colorless crystals of melting point 127°–128° C. Total yield: 24.8 g (82.6%) of 5-(1-hydroxy-4-oxo-2,6,6-trimethyl-2-cyclohexenyl)-3-methyl-2Z,4E-pentadien-1-ol.

EXAMPLE 5

14.5 g of 5-(1-methoxy-1-methylethoxy)-3-methyl-3E-penten-1-yne(96%, 83 mmol) were dissolved in 90 ml of tetrahydrofuran in a sulfonation flask provided with a stirrer, thermometer and dropping funnel with pressure balance while gassing with argon and cooled with an acetone/dry-ice bath to −15° C. At this temperature there were added while cooling well within 15 minutes 60 ml of a 1.4M solution of butyl lithium (80 mmol) in hexane and the resulting lithium salt solution was stirred at 0° C. for a further 30 minutes. A solution of 12.6 g of 2,6,6-trimethyl-3-isobutoxycyclohex-2-en-1-one (60 mmol) in 50 ml of tetrahydrofuran was subsequently added dropwise to the reaction mixture within 10 minutes while stirring, gassing with argon and cooling at −10° C. The cooling bath was then removed and the reaction mixture was warmed carefully to room temperature and stirred for 1 hour.

The reaction mixture was cooled to −10° C. Subsequently, 34 ml of a 70% (wt. %) solution of sodium bis(2-methoxyethoxy)aluminium hydride (120 mmol) in toluene were treated with 60 ml of tetrahydrofuran and the solution obtained was added dropwise to the reaction mixture within 10 minutes. The cooling bath was then removed with the reaction mixture was warmed carefully to room temperature and stirred for 2 hours.

Subsequently, the reaction mixture was treated dropwise with 30 ml of ethanol at −10° C. within 5 minutes, then treated with 200 ml of 3N sulphuric acid at about −10° C. to +5° C. and stirred at about 5° C. for a further 2 hours. Three separating funnels $S_1$–$S_3$ were each charged with 150 ml of ethyl acetate. Then, firstly the reaction mixture and then three 150 ml portions of saturated sodium hydrogen carbonate solution were passed in sequence and with good intermixing through the separating funnels $S_1$–$S_3$. The aqueous phases were discarded. The organic phases were combined and dried over sodium sulphate. The drying agent was filtered off and rinsed with 80 ml of ethyl acetate. The filtrate was evaporated in a rotary evaporator under a water-jet vacuum at 40° C. and finally largely freed from 3-methyl-2E-penten-4-yn-1-ol in a high vacuum (2 hours at 50° C./0.1 mm Hg). As the residue there were obtained 17.8 g of crude 3-[5-hydroxy-3-methyl-1E,3E-pentadienyl]-2,4,4-trimethyl-2-cyclohexen-1-one in the form of a yellowish oil. The oil obtained was chromatographed over 430 g of silica gel with n-hexane/ether (2:1). The product-containing fractions were combined and concentrated on a rotary evaporator at 40° C. under a water-jet vacuum. After drying in a high vacuum at room temperature, there were obtained 10.2 g (72.5% based on 2,6,6-trimethyl-3-isobutoxycyclohex-2-en-1-one) of 3-[5-hydroxy-3-methyl-1E,3E-pentadienyl]-2,4,4-trimethyl-2-cyclohexen-1-one which was pure according to thin-layer chromatography.

EXAMPLE 6

24.0 g of 3-methyl-2E-penten-4-yn-1-ol (249.6 mmol) were dissolved in 150 ml of absolute tetrahydrofuran in a sulfonation flask provided with a stirrer, thermometer and dropping funnel with pressure balance while gassing with argon and the solution was cooled with an acetone/dry-ice bath to −20° C. At this temperature there were added dropwise while cooling well within 15 minutes 308 ml of a 1.56M solution of butyl lithium (481.2 mmol) in hexane and the resulting dilithium salt (a beige suspension) was stirred at −10° C. under argon for a further 15 minutes. A solution of 25.2 g of 7,7a-dihydro-2,2,4,6,6-pentamethyl-1,3-benzo-dioxol-5(6H)-one (120 mmol) in 150 ml of tetrahydrofuran was subsequently added dropwise to the reaction mixture within 10 minutes while stirring, gassing with argon and cooling at −20° C. 2 g of tetrabutylammonium bromide (6.2 mmol) were then added to the reaction mixture, the cooling bath was removed and the mixture was warmed carefully to room temperature and stirred for 3 hours.

The reaction mixture was cooled to −30° C. Subsequently, 60 ml of a 70% solution of sodium bis(2-methoxy-ethoxy)aluminium hydride (215 mmol) in toluene were treated with 110 ml of tetrahydrofuran and the solution obtained was added dropwise to the reaction mixture within 10 minutes. The cooling bath was then removed and the reaction mixture was warmed carefully to room temperature and stirred for 1 hour.

Subsequently, the reaction mixture was treated dropwise with 100 ml of ethanol at −20° C. within 15 minutes, then treated with 500 ml of 3N sulfuric acid at about −10° C. to 15° C. and stirred at 15° C. to room temperature for a further 30 minutes. Three separating funnels $S_1$–$S_3$ were each charged with 400 ml of ethyl acetate. Then, firstly the reaction mixture and then three 250 ml portions of saturated sodium hydrogen carbonate solution were passed in sequence and with good intermixing through the separating funnels $S_1$–$S_3$. The aqueous phases were discarded. The organic extracts were combined and dried over sodium sulphate. The drying agent was filtered off and rinsed with 80 ml of ethyl acetate. The filtrate was concentrated in a rotary evaporator under a water-jet vacuum at 40° C. The residue obtained (44.8 g of a yellowish oil) was chromatographed on silica gel with diethyl ether/hexane (vol. 2:1). From the product-containing fractions there could be isolated 22.5 g (75.0%) of 6-hydroxy-3-(5-hydroxy-3-methyl-1E,3E-pentadienyl)-2,4,4-trimethyl-2-cyclohexen-1-one as colorless crystals of melting point 85°–86° C.

EXAMPLE 7

24.0 g of 3-methyl-2Z-penten-4-yn-1-ol (249.6 mmol) were dissolved in 150 ml of absolute tetrahydrofuran in a sulfonation flask provided with a stirrer, thermometer and dropping funnel with pressure balance while gassing with argon and the solution was cooled with an acetone/dry-ice bath to −20° C. At this temperature there were added dropwise while cooling well within 35 minutes 308 ml of a 1.56M solution of butyl lithium (481.2 mmol) in hexane and the resulting dilithium salt (a beige suspension) was stirred at −10° C. under argon for a further 20 minutes. A solution of 4(R)-(1-methoxy-1-methylethoxy)-2,2,6(R)-trimethylcyclohexan-1-one in absolute tetrahydrofuran was subsequently added dropwise to the reaction mixture within 10 minutes while stirring, gassing with argon and cooling at −15° C. 2 g of tetrabutylammonium bromide (6.2 mmol) were then added to the reaction mixture, the cooling bath was removed and the mixture was warmed carefully to room temperature and stirred for 3 hours.

The reaction mixture was cooled to −40° C. Subsequently, 60 ml of a 70% solution of sodium bis(2-methoxy-ethoxy)aluminium hydride (215 mmol) in toluene were treated with 110 ml of tetrahydrofuran and the solution obtained was added dropwise to the reaction mixture within 15 minutes. The cooling bath was then removed and the reaction mixture was warmed carefully to +5° C. and stirred for 1 hour.

Subsequently, the reaction mixture was treated dropwise with 100 ml of ethanol at −30° C. within 15 minutes, then treated with 300 ml of semi-saturated aqueous ammonium chloride solution at −15° C. to +5° C. and stirred at about 5° C. for a further 1 hour. Three separating funnels $S_1$–$S_3$ were each charged with 300 ml of ethyl acetate. Then, firstly the reaction mixture and then three 200 ml portions of semi-saturated aqueous sodium chloride solution were passed in sequence and with good intermixing through the separating funnels $S_1$–$S_3$. The aqueous phases were discarded. The organic phases were combined and dried over sodium sulphate. The drying agent was filtered off and rinsed with 80 ml of ethyl acetate. The filtrate was concentrated in a rotary evaporator under a water-jet vacuum at 40° C. 51.3 g of a yellowish oil were obtained as the residue.

The oil obtained was dissolved in 200 ml of tetrahydrofuran and 10 ml of deionized water in a flask provided with a thermometer, magnetic stirrer and argon gasification. After adding 1.0 g of pyridinium (toluene-4-sulfonate) (4 mmol), the reaction mixture was stirred at room temperature for 1 hour and subsequently poured into 300 ml of saturated sodium hydrogen carbonate solution in a separating funnel $S_1$. Separating funnels $S_2$–$S_3$ were each charged with 200 ml of ethyl acetate. Now, the aqueous phase from $S_1$ was passed with intensive intermixing through the separating funnels $S_2$–$S_3$ and subsequently discarded. The combined organic phases from $S_1$–$S_3$ were dried over sodium sulphate. The drying agent was filtered off and rinsed with 80 ml of ethyl acetate. The filtrate was concentrated in a rotary evaporator under a water-jet vacuum at 40° C. The residue obtained (40.3 g of a yellowish oil) was chromatographed on silica gel with diethyl ether/hexane (vol. 3:1). From the product-containing fractions there could be isolated 27.3 g (89.5%) of 5-[1(R,S),4(R)-dihydroxy-2,2,6(R)-trimethylcyclohexyl]-3-methyl-2Z,4E-pentadien-1-ol as a mixture of the two 1R/1S isomers.

The solution of 4(R)-(1-methoxy-1-methylethoxy)-2,2,6(R)-trimethylcyclohexan-1-one in tetrahydrofuran used above was prepared as follows:

A solution of 18.75 g of 4(R)-hydroxy-2,2,6(R)-trimethylcyclohexan-1-one (120 mmol) in 100 ml of tetrahydrofuran was placed in a sulfonation flask provided with a stirrer, thermometer and dropping funnel with pressure balance and cooled to 15° C. while gassing with argon and stirring. After adding 100 mg of pyridinium (toluene-4-sulfonate), 17.4 g of isopropenyl methyl ether (240 mmol) were added dropwise at 15°–25° C. within 30 minutes. The resulting solution of 4(R)-(1-methoxy-1-methylethoxy)-2,2,6(R)-trimethylcyclohexan-1-one was cooled to −10° C. and stored under argon until used.

EXAMPLE 8

56.4 g of 5-(1-methoxy-1-methylethoxy)-3-methyl-3E-penten-1-yne (97%, 325 mmol) were dissolved in 300 ml of absolute hexane in a sulfonation flask provided with a stirrer, thermometer and dropping funnel while gassing with argon and the solution was cooled with an acetone/dry-ice bath to 10° C. At this temperature there were added dropwise while stirring well within 15 minutes 192.3 ml of a 1.56M solution of butyl lithium (300 mmol) in hexane. The reaction mixture was stirred at 10° C. for a further 1 hour and then warmed to room temperature. A solution of 52.7 g of 7,7a-dihydro-2,2,4,6,6-penta-methyl-1,3-benzodioxol-5(6H)-one (250 mmol) in 120 ml of hexane was subsequently added dropwise to the reaction mixture within 15 minutes and the resulting mixture was stirred at room temperature for a further 3 hours.

The reaction mixture was cooled to −40° C. Subsequently, 107.1 ml of a 70% solution of sodium bis(2-methoxyethoxy)aluminium hydride (375 mmol) in toluene were added to the reaction mixture within 10 minutes. The reaction mixture was then warmed slowly to 0° C., kept at this temperature for 2 hours and subsequently stirred at room temperature for 16 hours.

Subsequently, the reaction mixture was treated with 250 ml of ethanol at −20° C. within 20 minutes, then treated with 500 ml of semi-saturated ammonium chloride solution at −20° C. to +10° C. and stirred well. Three separating funnels S₁-S₃ were each charged with 1 l of ethyl acetate. Then, firstly the reaction mixture and then one 500 ml portion of semi-saturated ammonium chloride solution and two 1 l portions of semi-saturated sodium chloride solution were passed in sequence and with good intermixing through the separating funnels S₁-S₃. The aqueous phases were discarded. The organic phases were combined, dried over sodium sulphate and filtered. The filtrate was concentrated in a rotary evaporator under a water-jet vacuum at 40° C. and dried under a high vacuum at 50° C. for 2 hours. The residue (100.9 g) was dissolved in 1 l of tetrahydrofuran and 100 ml of water and treated with 2.5 g of p-toluene sulfonic acid. The solution was stirred at room temperature for 30 minutes while gassing with argon and then poured on 500 ml of ethyl acetate placed in a separating funnel S₁. Separating funnels S₂ and S₃ were each charged with 500 ml of ethyl acetate. Then, two 750 ml portions of saturated sodium hydrogen carbonate solution were passed with good intermixing through the separating funnels S₁-S₃. The aqueous phases were discarded. The organic phases were combined, dried over sodium sulphate and filtered. The filtrate was concentrated in a rotary evaporator under a water-jet vacuum at 40° C. and finally dried under a high vacuum at 50° C. for 5 hours. The residue obtained (69.9 g, purity 78%, yield 86%) was chromatographed over silica gel with diethyl ether/hexane (vol. 2:1). From the product-containing fractions there were obtained 48.2 g (77%) of 6-hydroxy-3-(5-hydroxy-3-methyl-1E,3E-pentadienyl)-2,4,4-trimethyl-2-cyclohexen-1-one as colorless crystals of melting point 85°-86° C.

We claim:

1. A process for producing a 3-methyl-2,4-pentadien-1-ol derivative of the formula:

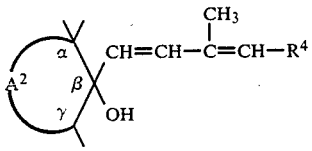

wherein $R^4$ is —CHR²R³, —CH₂OH or —CHO, $R_2$ is hydrogen or an ether group, $R_3$ is an ether group or the two ether groups of $R^2$ and $R^3$ together represent a cyclic diether group, $A^2$ is a chain of 2 or 3 carbon atoms which can be optionally substituted by 1 or 2 hydroxy or ether groups or a geminal or vicinal cyclic diether group or an oxo group and the ends of the carbon chain $A^2$ are linked with the carbon atoms in the α- and γ-positions, from a cyclic ketone of the formula:

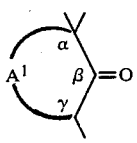

wherein $A^1$ is a chain of 2 or 3 carbon atoms which can be optionally substituted by 1 or 2 ether groups or a geminal or vicinal cyclic diether group, the ends of the chain being linked with the carbon atoms in the α- and γ-positions, comprising (a) reacting said cyclic ketone with a lithium salt of the formula:

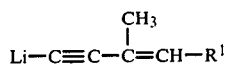

wherein $R_1$ is CHR²R³ or CH₂OLi and $R_2$ and $R_3$ are as above in an inert organic solvent to produce a alkoxide of the formula:

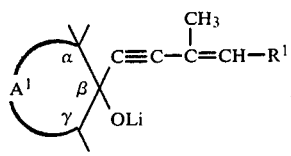

wherein $A^1$ and $R^1$ are as above;

(b) reducing said alkoxide with an aluminum hydride of the formula:

wherein Me is an alkali metal, x is a number of from 1 to 3 and m and n each are a number of from 1 to 7 to produce an aluminium complex of said 3-methyl-2,4-pentadien-1-ol derivative; and (c) hydrolyzing said aluminium complex to produce said 3-methyl-2,4-pentadien-1-ol derivative.

2. The process of claim 1, wherein $A^1$ is —CH₂—CH=, —CH₂—CH₂—CH₂—, —CH₂—CH₂—CH= or —CH=CH—CH= or a group derived therefrom in which 1 or 2 hydrogen atoms have been replaced by hydroxy or oxo groups protected by a hydrolyzable ether group.

3. The process of claim 2, wherein $A^1$ is the group —CHR—CR'=, —CH₂—CR=, —CH₂—CH₂—CH₂—, —CH₂—CHR—CH₂—, —CH₂—CR-R'—CH₂—, —CH₂—CH₂—CR=, —CH₂—CHR—CR'= or —CH₂—CRR'—CH= in which R and R' are individually hydroxy protected with a hydrolyzable ether group or taken together form oxo protected by a hydrolyzable ether group.

4. The process of claim 1 wherein the ether group which is present in $A^1$ is formed from hydroxy etherified with methoxy, isobutoxy or 1-methoxy-1-methylethoxy or oxo etherified with ethylenedioxy or two vicinal hydroxy groups etherified by means of an acetonide or a protected enolyzed α-hydroxy ketone etherified by means of forming a dimer.

5. The process of claim 1 wherein the ether groups present in $R^1$ are methoxy, isobutoxy or 1-methoxy-1-methylethoxy or the two ether groups together also represent ethylenedioxy.

6. The process of claim 1 wherein $R^1$ is —CH₂OLi.

7. The process according to claim 1 wherein Me represents lithium or sodium and x represents the number 2.

8. The process according to claim 7 wherein the reduction is carried out with sodium bis(2-methoxyethoxy)aluminium hydride.

9. The process of claims 1 wherein steps (a), (b) and (c) are carried out in an ether or a saturated or aromatic hydrocarbon solvent.

10. The process of claim 9, wherein the reaction is carried out in tetrahydrofuran.

11. A process of forming a hydroxy compound of the formula:

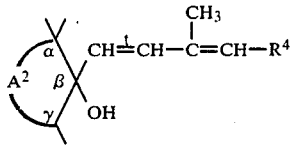

wherein $A^2$ is a chain of 2 or 3 carbon atoms, optionally substituted by 1 or 2 hydroxy or ether groups; or an oxo group and the ends of the chain being linked with the carbon atoms in the α- and γ-positions; and $R^4$ is —CH—$R^2R^3$, —CH$_2$OH or CHO, $R_2$ is hydrogen or hydroxy protected by a hydrolyzable ether group; and $R^3$ is an ether group and t designates a trans configuration;
comprising reducing a compound of the formula:

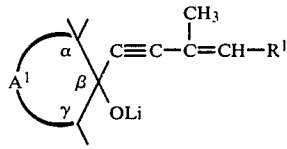

wherein $A^1$ is a chain of 2 or 3 carbon atoms which may be optionally substituted by 1 or 2 ether groups, the ends of the chain being linked with the carbon atoms in the α- and γ-positions, $R^1$ is —CH$_2R^2R^3$ or CHOLi and $R^2$ and $R^3$ are as above with an aluminum hydride of the formula $$(C_nH_{2n+1}-O-C_mH_{2m}O)_x MeAlH_{4-x} \qquad IV$$

wherein Me represents an alkali metal, x represents a number of 1 to 3 and m and n each represent a number of 1 to 7,
and thereafter hydrolyzing the resulting product to form said hydroxy compound.

12. The process according to claim 11 wherein Me is lithium or sodium and x is 2.

13. The process according to claim 12 wherein the reduction is carried out with sodium bis(2-methoxyethoxy)-aluminium hydride.

* * * * *